(12) United States Patent
Worrel et al.

(10) Patent No.: US 8,298,185 B2
(45) Date of Patent: Oct. 30, 2012

(54) RETRACTABLE CANNULA FOR SURGICAL PROCEDURES

(75) Inventors: Daniel A. Worrel, Dallas, TX (US); Joshua S. Redstone, Dallas, TX (US)

(73) Assignee: Suremka Medical, LLC, Dallas, TX (US)

( * ) Notice: Subject to any disclaimer, the term of this patent is extended or adjusted under 35 U.S.C. 154(b) by 226 days.

(21) Appl. No.: 12/882,030

(22) Filed: Sep. 14, 2010

(65) Prior Publication Data

US 2012/0065589 A1  Mar. 15, 2012

(51) Int. Cl.
*A61M 5/178* (2006.01)
(52) U.S. Cl. .................................. 604/164.01
(58) Field of Classification Search .......... 604/104–107, 604/164.04; 600/235; 606/198
See application file for complete search history.

(56) References Cited

U.S. PATENT DOCUMENTS

| | | | | |
|---|---|---|---|---|
| 3,039,468 | A | * | 6/1962 | Price .............................. 604/540 |
| 5,279,564 | A | * | 1/1994 | Taylor ............................ 604/104 |
| 5,330,501 | A | * | 7/1994 | Tovey et al. .................... 606/198 |
| 5,411,517 | A | * | 5/1995 | Guignard ........................ 606/198 |
| 5,779,697 | A | | 7/1998 | Glowa et al. |
| 5,895,351 | A | | 4/1999 | Nottage et al. |
| 6,007,487 | A | | 12/1999 | Foley et al. |
| 6,228,063 | B1 | * | 5/2001 | Aboul-Hosn ................. 604/174 |
| 6,312,443 | B1 | | 11/2001 | Stone |
| 6,402,722 | B1 | | 6/2002 | Snow et al. |
| 6,565,536 | B1 | * | 5/2003 | Sohn .............................. 604/174 |
| 6,669,708 | B1 | * | 12/2003 | Nissenbaum et al. ......... 606/153 |
| 6,780,168 | B2 | * | 8/2004 | Jellie ............................. 604/107 |
| 6,929,621 | B2 | * | 8/2005 | Whitmore et al. ............ 604/109 |
| 7,037,321 | B2 | * | 5/2006 | Sachdeva et al. ............. 606/200 |
| 7,083,595 | B2 | | 8/2006 | Chu et al. |
| 7,131,985 | B1 | * | 11/2006 | Manhes ......................... 606/185 |
| 7,604,648 | B2 | * | 10/2009 | Kerr ............................... 606/198 |
| 7,935,127 | B2 | * | 5/2011 | Rosenberg et al. ........... 606/108 |
| 8,105,236 | B2 | * | 1/2012 | Malandain et al. ........... 600/219 |
| 2004/0039400 | A1 | | 2/2004 | Schmieding et al. |
| 2007/0016287 | A1 | * | 1/2007 | Cartledge et al. ............ 623/2.11 |
| 2007/0088259 | A1 | * | 4/2007 | Chu et al. ...................... 604/104 |
| 2008/0086165 | A1 | | 4/2008 | Lyon et al. |
| 2008/0242930 | A1 | * | 10/2008 | Hanypsiak et al. ........... 600/114 |
| 2009/0234398 | A1 | * | 9/2009 | Chirico et al. ............... 606/86 R |
| 2010/0240959 | A1 | * | 9/2010 | Donahue ....................... 600/204 |
| 2011/0092912 | A1 | * | 4/2011 | Li et al. ......................... 604/175 |
| 2011/0218565 | A1 | * | 9/2011 | Criscuolo ..................... 606/192 |

* cited by examiner

*Primary Examiner* — Nicholas Lucchesi
*Assistant Examiner* — Diva K Chander
(74) *Attorney, Agent, or Firm* — Steven H. Washam; Harper Washam LLP (57) ABSTRACT

A cannula assembly having a plurality of outwardly-biased flexible fins capable of inward movement such that the fins converge upon insertion of a trocar device. The fins include a slot formed therein, with a corresponding raised feature on the trocar shaft capable of engaging the slots. Inward movement of the trocar within the cannula lumen causes the fins to converge. An additional embodiment utilizes outwardly-biased flexible fins that lock together in a closed position, with corrugated features in the fin inner surface that contact the trocar shaft such that, upon insertion of the trocar, the fins unlock and splay outward.

24 Claims, 7 Drawing Sheets

RETRACTABLE CANNULA FOR SURGICAL PROCEDURES

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

1. Field of the Invention

The present invention relates to devices for performing percutaneous surgeries and, more specifically, to surgical cannulae.

2. Description of Related Art Including Information Disclosed Under 37 CFR 1.97 and 1.98

Traditional minimally-invasive arthroscopic surgeries are performed using a cannula device to penetrate small incisions in the patient's skin and outer tissue, creating a port through which surgical tools may be passed to allow access to the underlying structure of interest. For example, in shoulder arthroscopy, the procedure is performed through "portals" in the patient's skin. These portals are formed from small incisions, generally about ½ of an inch to an inch long in the skin, and are located over particular areas of the joint that the surgeon will need to operate upon. Cannulas are then inserted into the portals so that instruments can easily be placed in the shoulder joint. Shoulder arthroscopy itself involves inserting a specially designed video camera with a very bright fiber optic light source into the shoulder joint so that the important parts of the joint can be seen. Instruments that have been specially designed to remove inflamed tissue, attach sutures to bone, and repair tears and damaged tendons are then used to operate inside the shoulder.

The area between the skin tissue and shoulder joint is quite small. Consequently, it is necessary to "inflate" the area by pumping saline fluids into the joint under pressure. This pressure pushes the tissue outward from the joint and allows greater room for manipulation of the arthroscopic camera and other surgical tools. However, the actual working angle of the tools is ultimately determined by the length and inner diameter of the cannula. Heavy patients or patients with large amounts of skin and other tissue covering the joint require a longer cannula to penetrate the tissue sufficiently for the procedure. This increased cannula length decreases the working angle of the tools at the joint, limiting the ability of the surgeon to perform the procedure. Although this angle may be increased by increasing the inner diameter of the cannula, there are realistic limits on the useable diameter. For example, the diameter can only be increased by a small amount or else it would effectively eliminate any benefit of conducting the arthroscopic procedure as the portal size could become the equivalent of a large incision as performed in traditional surgery.

What is needed is a cannula device that is capable of compressing the tissue through which it penetrates, and that is relatively simple to insert and remove so as to minimize tissue damage to the patient.

BRIEF SUMMARY OF THE INVENTION

A cannula assembly, the assembly comprising: a body member including a proximal end, a distal end, and a lumen extending therebetween, the distal end including a plurality of outwardly-biased flexible fins extending therefrom, each fin capable of inward movement such that the fins converge, each fin further including a wall formed from an inner surface and an edge surface extending from the inner surface to an outer surface, and at least one longitudinal slot formed within the fin wall and extending to a surface; and a trocar device including a proximal end and a shaft extending therefrom to form a distal end, the shaft member including at least one raised member per fin slot, each raised member being radially disposed proximate the distal end, the shaft member capable of insertion into the lumen, wherein insertion of the shaft within the lumen engages the raised members with the fin slots causing inward movement of the fins.

A cannula assembly, the assembly comprising: a body member including a proximal end, a distal end, and a lumen extending therebetween, the distal end including a plurality of outwardly-biased flexible fins extending therefrom, each fin capable of inward movement such that the fins converge, each fin further including a wall formed from an inner surface and an edge surface extending from the inner surface to an outer surface, and at least one longitudinal slot formed within the wall and edge surface; and a trocar device including a proximal end and a shaft extending therefrom to form a distal end, the shaft member including at least one raised member per fin slot, each raised member being radially disposed proximate the distal end, each raised member cross section approximating the shape the fin slots, the shaft member capable of insertion into the lumen, wherein insertion of the shaft within the lumen engages the raised members with the fin slots causing inward movement of the fins such that the fins converge.

A cannula assembly, the assembly comprising: a body member including a proximal end, a distal end, and a lumen extending therebetween, the distal end including a plurality of outwardly-biased flexible fins extending therefrom, one fin including a locking feature at its distal end, wherein the other fins may be captured beneath the locking feature closing off the lumen; a trocar device including a proximal end and a shaft member extending therefrom to form a distal end, the shaft member capable of insertion into the lumen; and an anti-plunging device removably attachable to the shaft member wherein the attached anti-plunging device blocks the shaft member from advancing past a first position within the lumen, and wherein removal of the anti-plunging device allows the shaft member to advance past the first position to a second position wherein the fins unlock and move outward.

BRIEF DESCRIPTION OF THE SEVERAL VIEWS OF THE DRAWING(S)

The present invention will be more fully understood by reference to the following detailed description of the preferred embodiments of the present invention when read in conjunction with the accompanying drawings, wherein.

The above figures are provided for the purpose of illustration and description only, and are not intended to define the limits of the disclosed invention. Use of the same reference number in multiple figures is intended to designate the same or similar parts. Furthermore, when the terms "top," "bottom," "first," "second," "upper," "lower," "height," "width," "length," "end," "side," "horizontal," "vertical," and similar terms are used herein, it should be understood that these terms have reference only to the structure shown in the drawing and are utilized only to facilitate describing the particular embodiment. The extension of the figures with respect to number, position, relationship, and dimensions of the parts to form the preferred embodiment will be explained or will be within the skill of the art after the following teachings of the present invention have been read and understood.

DETAILED DESCRIPTION OF THE INVENTION

Figure 1:
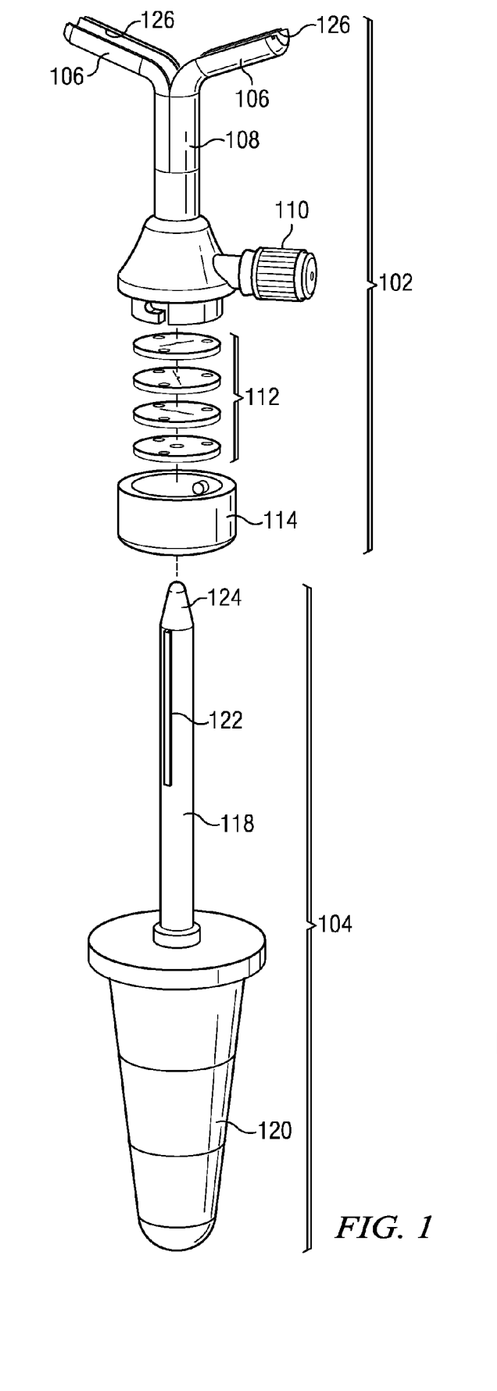
FIG. 1 is an exploded view of a first embodiment of the cannula invention.

FIG. 1 depicts an exploded view of a first embodiment of the cannula invention. As shown in this figure, the complete apparatus includes a cannula device (102) and a trocar device (120). The trocar device (104) includes a handle (120) at its proximal end with a shaft member (118) extending therefrom to form a distal end with a defined tip (124). Along the shaft are multiple raised members (122) that protrude essentially radially from the axial center of the shaft (118) and that extend longitudinally along the shaft length. The raised members (122) in the present embodiment are depicted as extending approximately one half of the length of the shaft (118) near the distal end. However, the length of the raised members (122) may vary in other embodiments. For example, the raised members (122) in another embodiment may be wider than they are in length. Such alternate lengths are within the scope of the present invention. The raised member (122) of the embodiment, as depicted, is also a single element. However, in another embodiment the raised member may be split in to portions such that, on the whole, the raised member (122) may still engage the corresponding slot.

The present embodiment of the cannula device (102) includes body member (108) having a proximal end and a distal end. The body member (108) is essentially cylindrical in shape, having a lumen extending from end to end. Although the body member in the present embodiment is essentially cylindrical in shape, other embodiments may have a geometric cross-sectional shape other than circular, or may include a mix of circular and other geometric shape such as a circular lumen cross section with a geometric outer wall cross section or vice versa. The outer wall may also include a ribbed, grooved, or helical raised feature (or even a recessed feature) that assists the device in gripping a patient's skin and muscle tissue for device retention. Such alternate embodiments are envisioned and are within the scope of the present invention.

The proximal end includes a fluid drain port (110) and a proximal collar (114) that retains several silicon discs (112) that are used as fluid seals through which surgical instruments may pass. The proximal collar (114) attaches to the proximal end of the body member for positive retention of the silicon discs (112). The drain port (110) allows for fluid management during surgical procedures in the same fashion as conventional cannula devices.

The distal end of the body member (108) includes a plurality of flexible, yet semi-rigid fins (106) that are formed in the outwardly-biased position as shown during injection molding of the device. The present embodiment utilizes medical grade polymers during the injection molding or extrusion process. These polymers allow the fins to retain the outwardly-biased shape at normal operating temperatures for the device, yet also allow the fins to flex inwardly when sufficient pressure is applied. For example, polyurethanes such as Hytrel/Arnitel may be utilized due to the desired durability characteristics, or PVC if expense is a concern.

Figure 2:
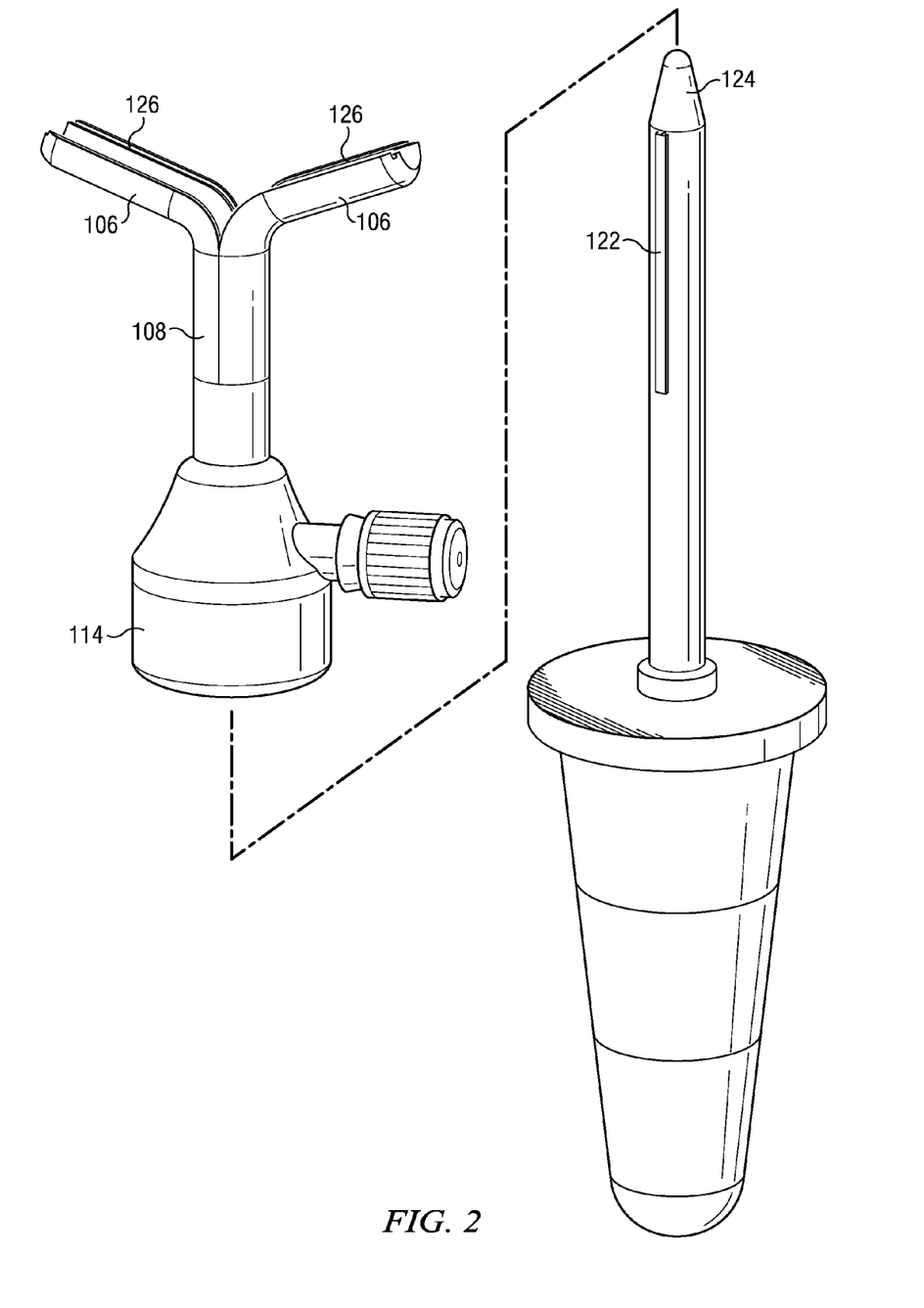
FIG. 2 is an assembled view of the embodiment, highlighting a cross sectional area.

Each fin (106) of the present embodiment includes a radius of curvature that approximates that of the wall of the body member (108) that forms the lumen. When the fins (106) are forcibly moved to the inward position (as depicted in FIG. 2), the inner surface of the fins essentially extends the lumen of the body member (108) to the distal end of the fins. Further, because the fins have a wall thickness, each fin features an edge surface that extends from the fin inner surface to the fin outer surface. It is the edge surface of the fin that contacts the edge surface of the adjacent fin when the fins are in the inward-most position (as in FIG. 2).

FIG. 2 depicts the cannula invention prior to insertion of the trocar device. As shown, the tip (124) of the trocar device is inserted through the cannula device proximal collar (114) such that the raised members (122) engage with complimentary slots formed within the body member (108) of the cannula device. These complimentary slots extend a distance within the cannula device lumen and along the edge surfaces (126) of the fins (106). This embodiment features two corresponding slots (126), one for each fin. Other embodiments may utilize a greater number of fins and, consequently, would require a correspondingly greater number of slots. For example, an embodiment with three outwardly-biased fins would have three pairs of adjacent fin edge surfaces. Such an embodiment would require three slots within the cannula body member and three corresponding complimentary raised members on the trocar device.

Figure 3:
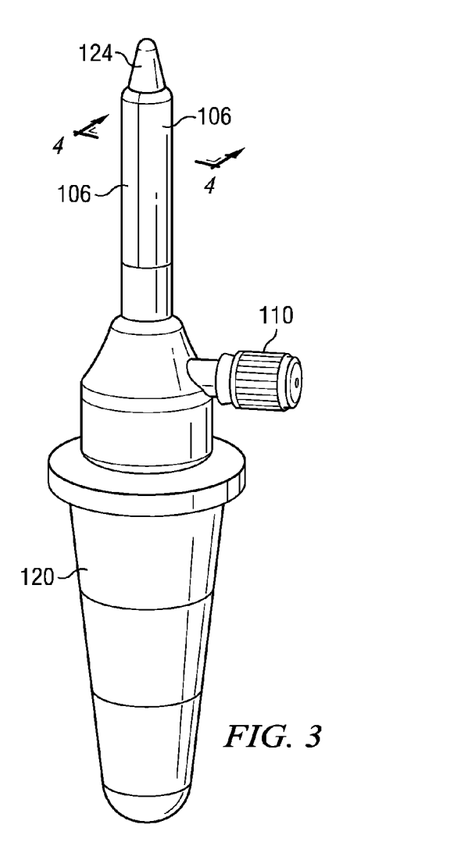
FIG. 3 is a cross section of the working end of the invention as in the assembled view of the embodiment.

FIG. 3 depicts an assembled view of the embodiment as it would be configured for use once the trocar device (120) is inserted into the cannula device body member (106). As shown, insertion of the trocar device (120) engages the slots within the fins (106), causing the fins (106) to move inward against the outward bias pressure that is normally present. In the full inward position the edge surfaces of the fins (106) meet. This figure also highlights a cross sectional area, which is shown in detail in FIG. 4.

Figure 4:
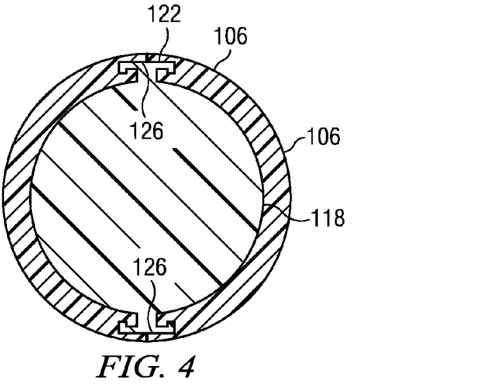
FIG. 4 is a depiction of the cannula invention prior to insertion of the trocar device.

The cross section detail depicted in FIG. 4 demonstrates how the trocar shaft member (118) fits within the cannula lumen and engages the complementary slots in the fins (106). In this embodiment, the cannula device has two fins. Formed within the inner wall of the body member are two slots, each having a cross section that resembles a serif font capital letter "T". This slot extends the length of the body member inner wall and is aligned with the origin of the edge surfaces of the fins (106) as they extend from the body member, and accepts a corresponding serif font capital letter "T" shaped raised member (122) on the trocar.

A corresponding portion of the "T" slot is formed in the wall of each fin at the junction of the edge surface and the inner surface. When the fins (106) are in the inward most (or "closed") position (as shown in FIG. 3), the adjoining fin edge surfaces (126) meet and complete the overall "T" slot such that it extends from the body member to the distal end of the fins. Although the corresponding "T" slot portion in the fin edge surfaces (126) extends approximately the entire length of the fin in the present embodiment, other embodiments may extend less than the entire length of the fin.

To prepare the embodiment for use with a patient, the trocar device is inserted into the cannula device lumen such that raised members (122) engage the corresponding and complimentary body member "T" slots. As the trocar shaft (118) is further inserted into the lumen, the raised members slide within the "T" slots until they reach the origin of the edge surfaces of the fins (106). As the trocar is further inserted, the raised members apply stress to the corresponding "tail" elements of "T" slot portions in each fin edge surface (126) causing the fins to move inward and come together along adjacent edge surfaces. This has the effect of "zipping" the fin edges together for insertion of the device into a patient.

Although a serif capital "T" shaped slot cross section is discussed, other embodiments may utilize cross-sectional slot shapes that provide an elemental feature that positively engages and accepts compressive stresses from the corresponding elements of the raised members to cause the fins to move inward and come together along adjacent edge surfaces as the trocar is inserted. Each fin edge surface may include a slot that features a cavity that is larger than the opening formed in the edge surface, with additional material removed from the edge surface where it intersects with the fin inner surface to allow for the corresponding raised member to pass therebetween. For example, the edge surface may have a longitudinal slot formed therein that has a dovetail cross section. The corresponding raised member would include two corresponding dovetail pin features to engage the adjacent dovetail slots in the adjacent fin edge surfaces. Each fin edge surface may also include a slot with a formed cavity that turns inward towards the inner surface, outward towards the outer surface, or both, such that the slot opening in the edge surface is not aligned with the deepest portion of the slot cavity. For example, the edge surface may have a longitudinal slot that is formed such that cavity beneath the slot opening is centered toward the inner surface and does not share the exact centerline of the cavity opening. Again, the trocar device would include a corresponding raised member that engages the slot as before. In yet another embodiment it is also possible to have a plurality of slots, with each slot having a different geometric cross sectional shape.

Figure 14:
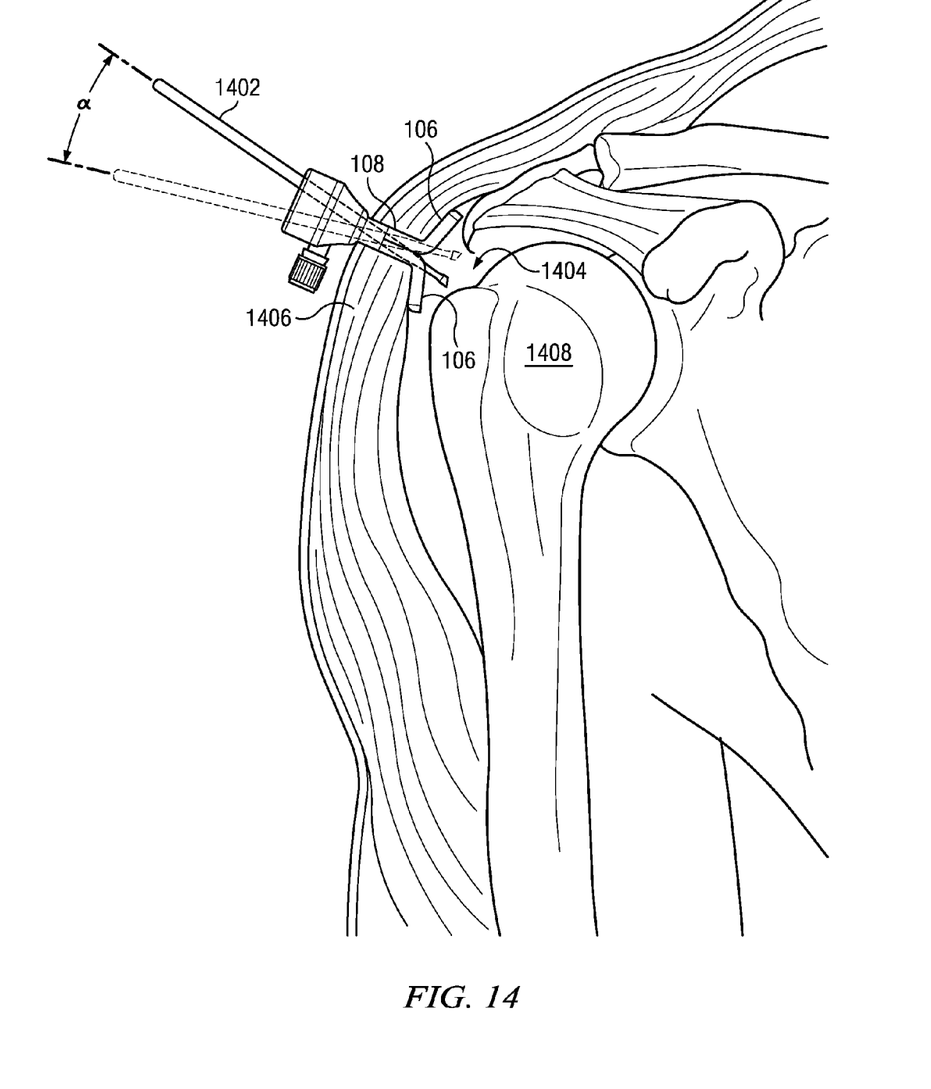
FIG. 14 is a cutaway view of the invention in use during shoulder surgery.

Once inside a patient, the trocar is removed from the cannula device and the fins naturally return to their outwardly-biased position. FIG. 14 depicts such an event. As shown, the body member (108) forms a port in the patient's skin and outer tissue (1406) through which surgical instruments (1402) may pass. The outwardly-biased flexible fins (106) of the cannula device exert pressure on the tissue (1406) and assist the surgeon in compressing the tissue (1406) to allow for a greater working cavity (1404) and exposure of the surgery site (1408). Because of the compressive effect of the flexible fins (106) on the tissue (1406), the length of the body member (108) may be made relatively short compared to conventional cannula devices. This shortened body member (108) results in a shortened lumen length that, consequently, allows a greater working angle (shown on the figure as the Greek letter "α") for the surgeon's tools (1402), which improves the surgeon's access to the surgery site and reduces the need for physical manipulation of the cannula during surgery. When surgery is complete, the cannula device may be removed by reinserting the trocar device into the lumen such that the trocar raised members engage the slots in the fins and the fins move inward once more. The cannula device may then be withdrawn from the patient with minimal tissue damage. Although the present embodiment is described in use during shoulder arthroscopy, one of ordinary skill will understand that the device may be employed in essentially any arthroscopic, laparoscopic, or other surgery requiring the surgeon to establish a working port in the tissue of a patient.

Figure 5:
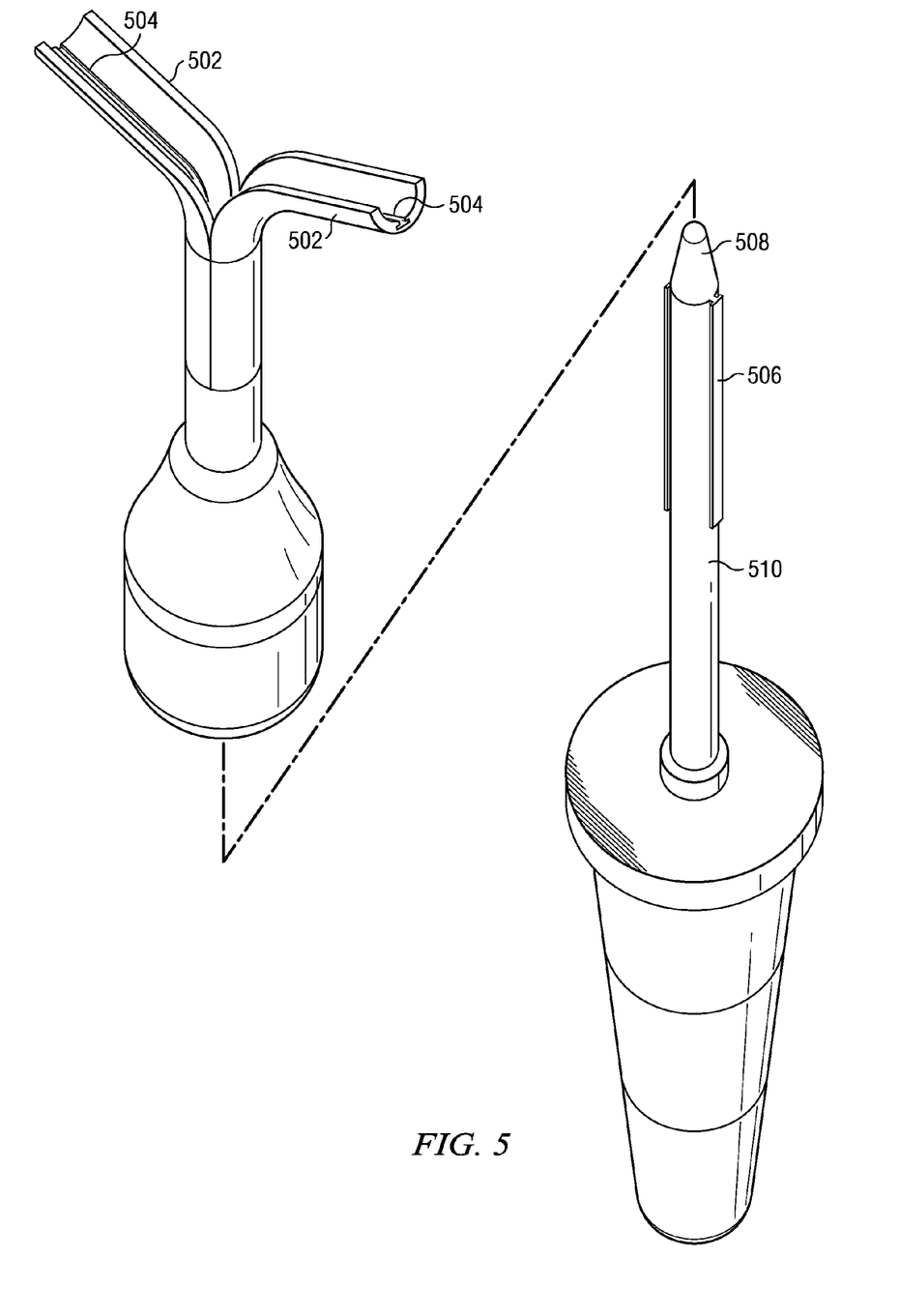
FIG. 5 is a depiction of an alternative embodiment of the cannula invention prior to insertion of the trocar device.
Figure 6:
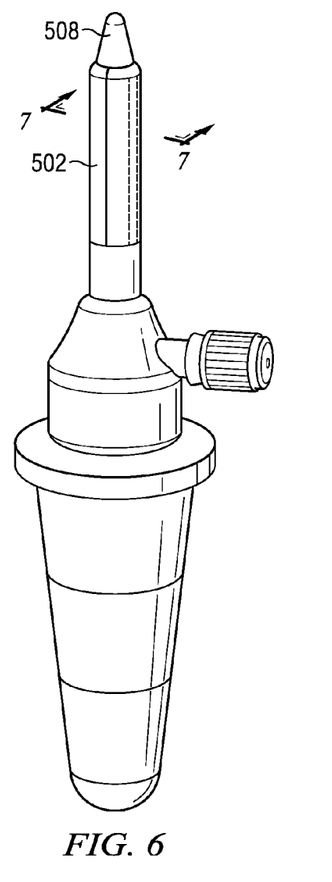
FIG. 6 is an assembled view of the alternative embodiment, highlighting a cross sectional area.

FIG. 5 depicts an alternative embodiment of the cannula invention prior to insertion of the trocar device. As shown, the trocar device has a shaft member (510) with raised members (506) and a distal tip (508). However, in this embodiment the corresponding slots in the cannula device are formed such that they extend from the proximal opening and along the inner wall of the body member and along the inner wall of the fins (502) at some point between each fin's edge surface (504). Insertion of the trocar device into the cannula device, once again, causes the flexible outwardly-biased fins 502) to move inward such that adjacent fin edge surfaces meet and the closed fins essentially form an extension of the body member as shown in FIG. 6. In this figure, the device is again ready for insertion into a patient.

Figure 7:
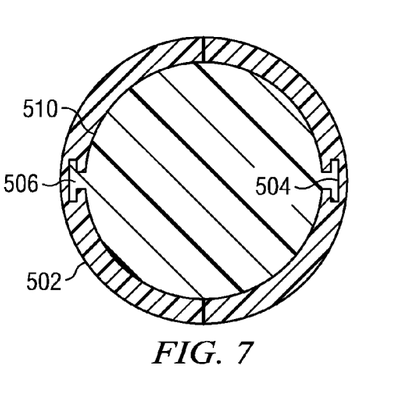
FIG. 7 is a cross section of the working end of the invention as in the assembled view of the alternative embodiment.
Figure 8:
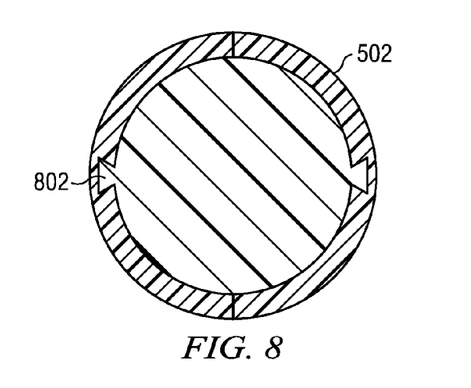
FIG. 8 is a cross section of the working end highlighting an alternative dovetail channel shape.
Figure 9:
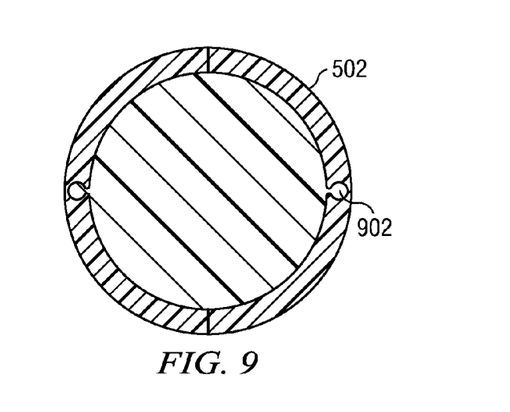
FIG. 9 is a cross section of the working end highlighting an alternative circular channel shape.

FIG. 6 depicts an assembled view of the alternative embodiment, highlighting a cross sectional area. FIG. 7 depicts the cross section of this embodiment in which conventional "T" slots (504) are formed in the fin (502) inner walls approximately midway between the edge surfaces. The trocar shaft (510) features raised members (506) that correspond with each "T" slot. Although the present embodiment depicts a single slot formed midway between the edge surfaces of each fin, other embodiments may utilize multiple slots per fin, with appropriate spacing between the slots. In such embodiments, the trocar shaft will feature corresponding raised members that engage the slots. Further, although the present embodiment describes use of "T" slots in the fins, other geometric slot shapes that afford positive engagement with corresponding raised members may be utilized. For example, FIG. 8 depicts use of dovetail slots (802) formed in the inner surfaces of the fins (502). Likewise, FIG. 9 depicts use of circular slots (902) formed in the inner surfaces of the fins (502). Still other geometric slot shapes are contemplated and are within the scope of the present invention. Further, it is possible to combine fin edge surface slots with inner surface slots. Such an arrangement may be helpful to more evenly distribute the closing forces applied to the fins during insertion of the trocar device and prevent distortion of the fins.

Figure 10:
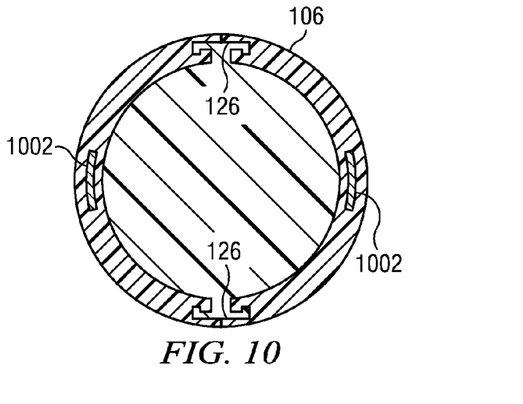
FIG. 10 is a cross section of the working end highlighting an alternative embodiment with an embedded material that assists in the open bias of the fins.

In yet another embodiment, it is possible to utilize an embedded shape memory alloy as a biasing device, such as but not limited to Nitinol, in each fin to increase the outward-bias pressure generated by the fins. By increasing the outward bias pressure, it is possible to apply additional compressive stress to the tissue of the patient through which the cannula device is inserted. FIG. 10 depicts such an embodiment. As shown, each fin (106) includes an embedded shape memory alloy strip (1002) within the fin wall at some location between the edge slots (126). This embedded shape memory alloy strip may also be used with the alternative embodiments discussed above, and may be incorporated within the wall beneath or near the respective slot. Further, although the figure depicts use of a single embedded shape memory alloy (1002) in each fin (106), other embodiments may utilize multiple shape memory alloys at various locations spaced within the fin walls. Other biasing devices may include other metals, such as stainless steel, or polymers that exert added biasing pressure over that provided by the molded fins.

In yet another embodiment it is possible to incorporate an additional alloy with the embedded shape memory alloy to create a bimetallic strip or alter the composition such that it varies, with temperature, the fin outward-bias pressure that is generated. For example, Nitinol may also be "tuned" to react at different temperatures by adding additional alloys to its composition. Such a material may be used in the fins of an embodiment to allow the fins to generate greater outward-bias pressures when the fins reach the patient's body temperature.

Figures 11, 12:
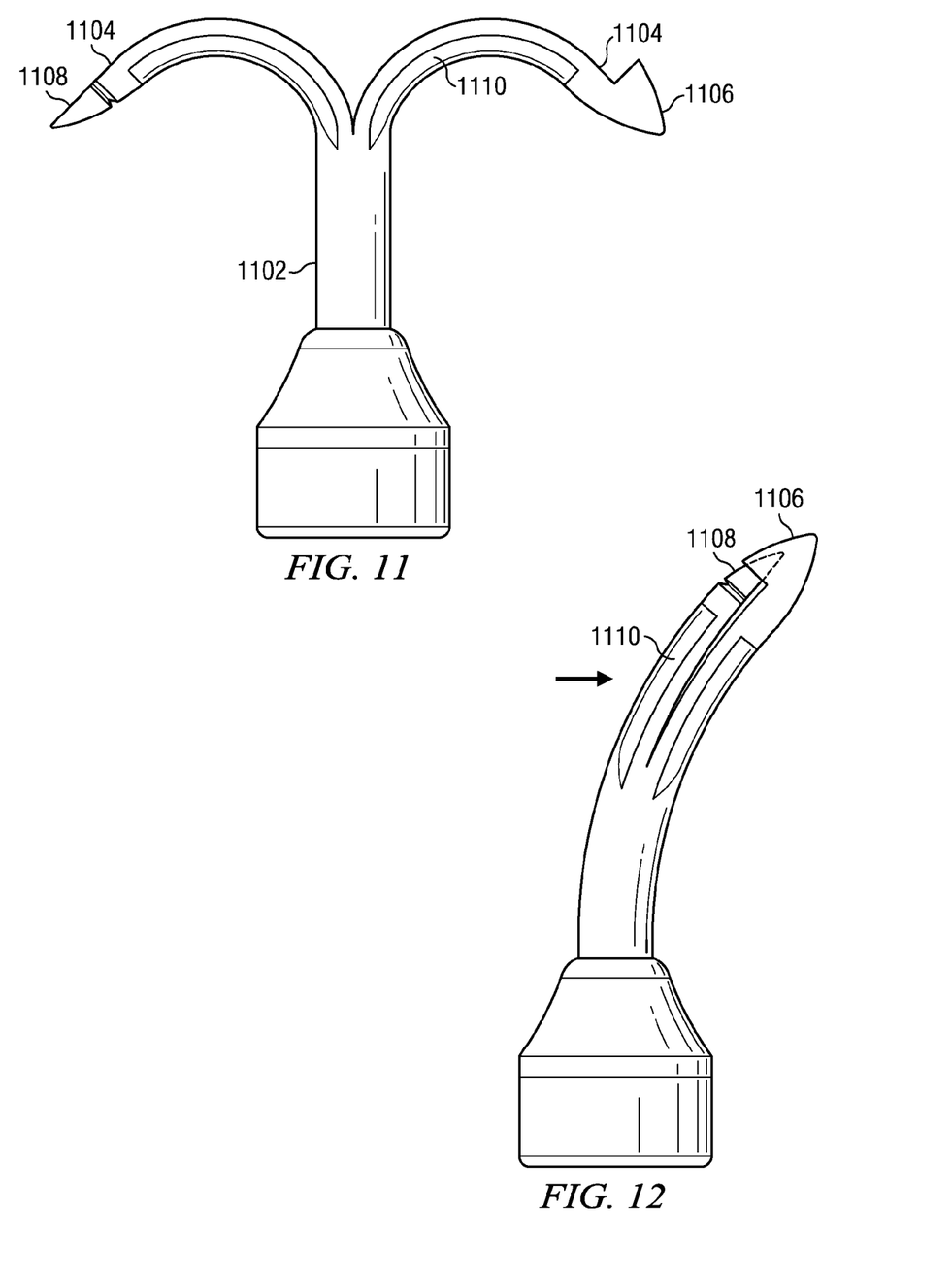
FIG. 11 is an alternative embodiment of the cannula invention with the fins in the open position.
FIG. 12 is a depiction of the process for closing the fins in the alternative embodiment.

FIG. 11 depicts an alternative embodiment of the cannula device of the present invention. As shown, the cannula device features a body member (1102) with a lumen that exists from the proximal end to the distal end, and a plurality of outwardly-biased fins (1104) extending from the distal end of the body member. Each fin includes a plurality of corrugated features (1110) that extend inward from the outer surface of the fin and are formed along the length of the fin. One fin includes a locking feature (1106) at its distal end for capturing the distal end of the other fins (1108). The locking feature in this embodiment is a conical portion of the distal end of the fin that allows the distal end of the other fins to be captured beneath.

This embodiment of the device is prepared as shown in FIG. 12. As depicted, the fins are physically moved inward such that the adjacent fin edges meet and a fin grouping is formed. The fin grouping is then bent toward the fin having the locking feature such that the fin with the locking feature is bent backward as depicted. The relative flexing of the fins in this fashion allows the fins without the locking feature (1108) to be inserted beneath the conical locking feature (1106) such that all are captured in the closed position as further depicted in FIG. 13.

Figure 13:
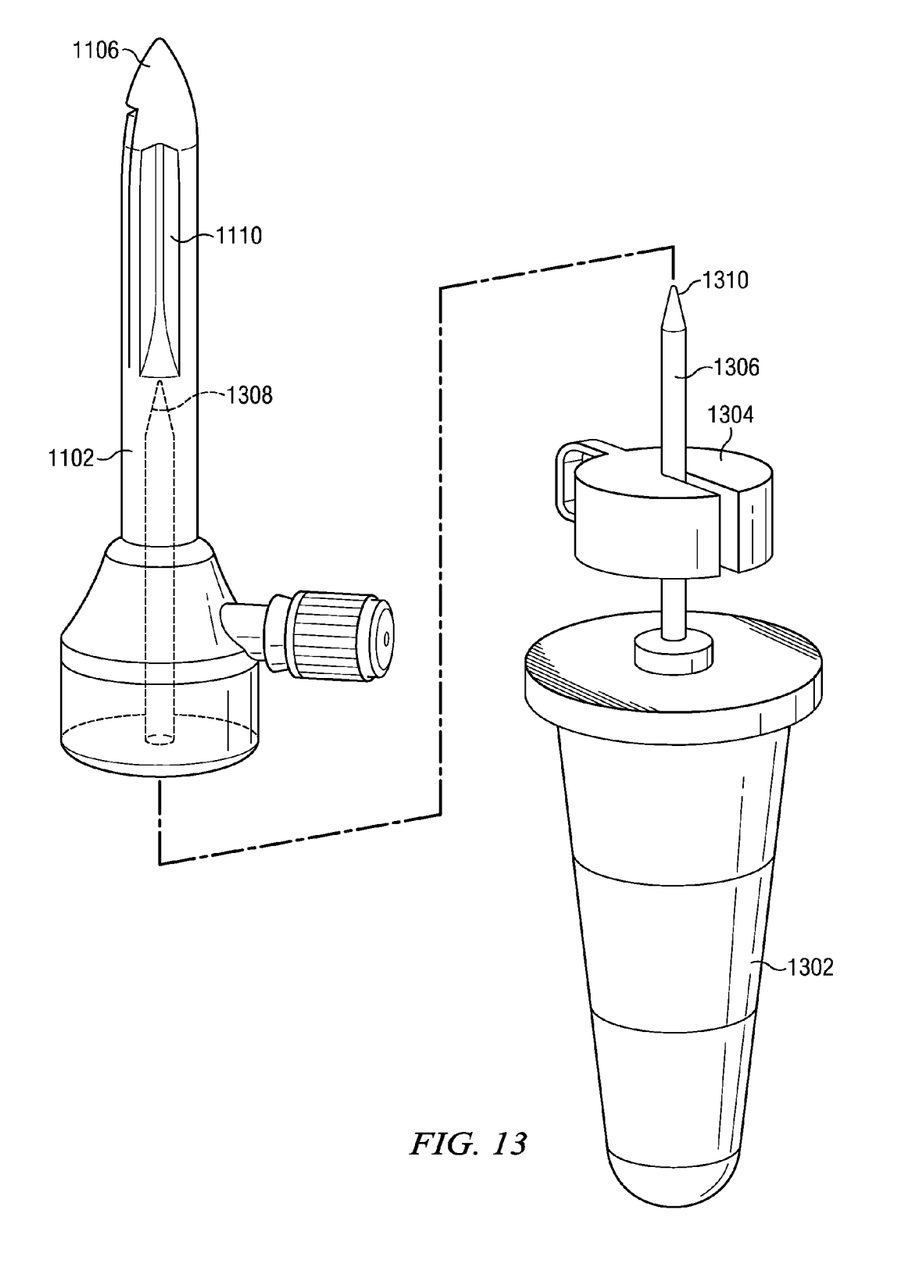
FIG. 13 is a depiction of the alternative embodiment of the cannula invention prior to insertion of the trocar device.

FIG. 13 depicts the additional elements of this embodiment as well as the prepared cannula device. As shown, the embodiment includes a trocar device having a handle (1302) with a shaft member (1306) extending from the proximal end to form a tapered distal end (1308). An anti-plunging device (1304) attaches to the shaft member (1306), and the tapered distal end (1308) is inserted into the proximal end of the cannula device lumen. The anti-plunging device (1304) blocks the shaft member distal end (1308) from advancing past a first position as shown in the figure by hidden lines in the body member (1102). This first position prevents the shaft member distal end (1308) from contacting the corrugated feature (1110) in the fins.

Once assembled, this embodiment may be utilized with a patient by inserting the distal end of the fin into an incision in the patient's skin Once the body member (1102) is fully inserted, the anti-plunging device (1304) is removed from the shaft (1306) and the trocar is further inserted past the first position to a second position. In the second position, the tapered distal end (1308) contacts the corrugated features (1110), applying force to the fins such that the captured fins are dislodged from beneath the locking feature (1106). The bias pressures of the fins then force the fins to return to the initial outward-bias position, compressing the patient's tissue through which the cannula device was inserted (as in FIG. 14).

The invention may be embodied in other specific forms without departing from the spirit or essential characteristics thereof. The present embodiments are therefore to be considered in all respects as illustrative and not restrictive. Accordingly, the scope of the invention is established by the appended claims rather than by the foregoing description. All changes which come within the meaning and range of equivalency of the claims are therefore intended to be embraced therein. Further, the recitation of method steps does not denote a particular sequence for execution of the steps. Such method steps may therefore be performed in a sequence other than that recited unless the particular claim expressly states otherwise.

We claim:

1. A cannula assembly, the assembly comprising:
a body member including a proximal end, a distal end, and a lumen extending therebetween, the distal end including a plurality of outwardly-biased flexible fins extending therefrom, each fin capable of inward movement such that the fins converge, each fin further including a wall formed from an inner surface and an edge surface extending from the inner surface to an outer surface, and at least one longitudinal slot formed within the fin wall and extending to a surface; and
a trocar device including a proximal end and a shaft extending therefrom to form a distal end, the shaft member including at least one raised member per fin slot, each raised member being radially disposed proximate the distal end, the shaft member capable of insertion into the lumen, wherein insertion of the shaft within the lumen engages the raised members with the fin slots causing inward movement of the fins.

2. The assembly of claim 1 wherein the slot is a T slot and the raised member cross section is a corresponding shape capable of engagement within the slot.

3. The assembly of claim 1 wherein the slot cross section is a geometric shape and the raised member cross section is a corresponding geometric shape capable of engagement within the slot.

4. The assembly of claim 1 wherein the slot is formed in the surface of the fins at the junction of the edge surface and the inner surface.

5. The assembly of claim 4 wherein the slots of adjacent fins form a T slot when the fins converge, and the raised member cross section is a corresponding shape capable of engagement within each pair of adjacent slots.

6. The assembly of claim 4 wherein the slots of adjacent fins form a cross section with a geometric shape when the fins converge, and the raised member cross section is a corresponding shape capable of engagement within each pair of adjacent slots.

7. The assembly of claim 1 wherein the longitudinal slot extends into the body member inner wall that forms the lumen.

8. The assembly of claim 1 wherein the raised member extends longitudinally a distance that is equal to or greater than the widest portion of the raised member.

9. The assembly of claim 1 wherein the body member wall is substantially cylindrical.

10. The assembly of claim 1 wherein the lumen is substantially cylindrical.

11. The assembly of claim 1 wherein each fin has a radius of curvature that approximates that of the lumen.

12. The assembly of claim 1, each fin further comprising: a biasing device within each fin wall.

13. The assembly of claim 12 wherein the biasing device is a shape memory alloy.

14. The assembly of claim 13 wherein the biasing device is capable of reacting to a patient's body temperature such that the biasing device outward biasing pressure increases.

15. A cannula assembly, the assembly comprising:
- a body member including a proximal end, a distal end, and a lumen extending therebetween, the distal end including a plurality of outwardly-biased flexible fins extending therefrom, each fin capable of inward movement such that the fins converge, each fin further including a wall formed from an inner surface and an edge surface extending from the inner surface to an outer surface, and at least one longitudinal slot formed within the wall and edge surface; and
- a trocar device including a proximal end and a shaft extending therefrom to form a distal end, the shaft member including at least one raised member per fin slot, each raised member being radially disposed proximate the distal end, each raised member cross section approximating the shape the fin slots, the shaft member capable of insertion into the lumen, wherein insertion of the shaft within the lumen engages the raised members with the fin slots causing inward movement of the fins such that the fins converge.

16. The assembly of claim 15 wherein each fin has a radius of curvature that approximates that of the lumen.

17. The assembly of claim 15, each fin further comprising: a biasing device within each fin wall.

18. The assembly of claim 17 wherein the biasing device is a shape memory alloy.

19. The assembly of claim 18 wherein the biasing device is capable of reacting to a patient's body temperature such that the biasing device outward biasing pressure increases.

20. A cannula assembly, the assembly comprising:
- a body member including a proximal end, a distal end, and a lumen extending therebetween, the distal end including a plurality of outwardly-biased flexible fins extending therefrom, one fin including a locking feature at its distal end, wherein the other fins may be captured beneath the locking feature closing off the lumen;
- a trocar device including a proximal end and a shaft member extending therefrom to form a distal end, the shaft member capable of insertion into the lumen; and
- an anti-plunging device removably attachable to the shaft member wherein the attached anti-plunging device blocks the shaft member from advancing past a first position within the lumen, and wherein removal of the anti-plunging device allows the shaft member to advance past the first position to a second position wherein the fins unlock and move outward.

21. The assembly of claim 20 further comprising a corrugated feature formed longitudinally along each fin such that the shaft member only contacts the corrugated feature in the second position.

22. The assembly of claim 20, each fin further comprising: a biasing device within each fin wall.

23. The assembly of claim 22 wherein the biasing device is a shape memory alloy.

24. The assembly of claim 23 wherein the biasing device is capable of reacting to a patient's body temperature such that the biasing device outward biasing pressure increases.

* * * * *